United States Patent [19]

Cywinski

[11] 4,271,315
[45] Jun. 2, 1981

[54] TREATMENT OF WASTE STREAM FROM ADIPIC ACID MANUFACTURE

[75] Inventor: Norbert F. Cywinski, Odessa, Tex.

[73] Assignee: El Paso Products Company, Odessa, Tex.

[21] Appl. No.: 94,427

[22] Filed: Nov. 15, 1979

[51] Int. Cl.³ .................. B01D 3/34; C07C 67/00
[52] U.S. Cl. .................. 560/204; 203/38; 203/43; 203/66; 203/DIG. 25
[58] Field of Search .................. 560/204, 191; 203/14, 203/15, 16, 43, 38, 39, DIG. 6, 66, DIG. 25; 159/47 R, 48 L; 210/21, 73

[56] References Cited

U.S. PATENT DOCUMENTS

| 2,824,122 | 2/1958 | Kuceski | 560/204 |
|---|---|---|---|
| 3,726,888 | 4/1973 | Hatten et al. | 560/204 |
| 3,810,937 | 5/1974 | Kuceski | 560/204 |
| 3,886,199 | 5/1975 | Suter et al. | 560/204 |
| 4,052,441 | 10/1977 | Brunner | 560/204 |
| 4,076,948 | 2/1978 | Mims | 560/204 |
| 4,082,788 | 4/1978 | Mims | 560/204 |
| 4,105,856 | 8/1978 | Newton | 560/204 |

*Primary Examiner*—Wilbur L. Bascomb, Jr.

[57] ABSTRACT

This invention provides a process for improving the recovery of byproducts associated with the isolation of $C_4$–$C_6$ dicarboxylic acids contained in a waste byproduct stream, derived from an adipic acid manufacturing operation wherein there is involved nitric acid oxidation of a cyclohexanone/cyclohexanol feedstream.

The main byproducts which are isolated are high purity dimethyl succinate, dimethyl glutarate and dimethyl adipate. Monomethyl esters of these dicarboxylic acids are recovered and recycled in the process.

13 Claims, 1 Drawing Figure

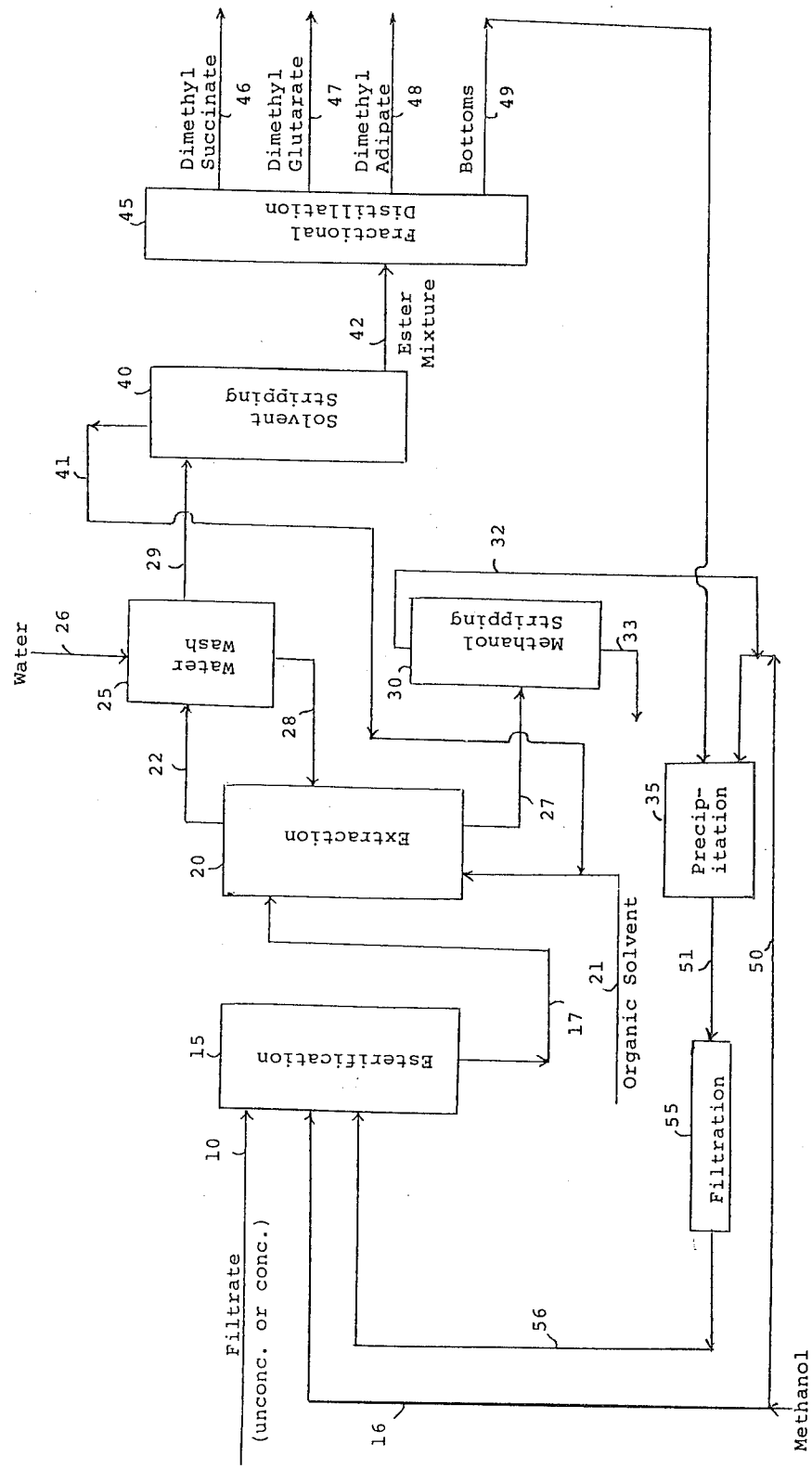

TREATMENT OF WASTE STREAM FROM ADIPIC ACID MANUFACTURE

BACKGROUND OF THE INVENTION

Adipic acid is an important intermediate for the production of nylon. Commerical methods for producing dicarboxylic acids generally involve oxidizing naphthenes, cycloaliphatic ketones or cycloaliphatic alcohols with nitric acid in the presence of metal oxidation catalysts.

In the case of adipic acid, specific feed materials such as cyclohexane, cyclohexanol and/or cyclohexanone in admixture with nitric acid are heated at about 40° C.–140° C. in the presence of a catalyst. The resultant oxidation reaction product comprises adipic acid together with small amounts of monocarboxylic acids and dicarboxylic acids and other organic components in admixture with nitric acid and catalyst components. A substantial quantity of the adipic acid product is recovered by cooling the solution and filtering off the crystallized adipic acid. Oxidation methods of adipic acid production are described in U.S. Pat. Nos. 2,439,513; 2,557,281; 2,791,566; 2,840,607; 2,971,010; 3,338,959; and references cited therein.

In a process involving nitric acid oxidation of cyclohexanone and/or cyclohexanol, economically significant amounts of succinic acid and glutaric acid are formed as byproducts in admixture with the adipic acid. After the major portion of the adipic acid is separated by crystallization and filtration, the filtrate mother liquor contains some adipic acid, as well as succinic acid, glutaric acid, nitric acid and metal catalyst values.

Usually this filtrate has been treated as a waste stream. Because of environmental and economic considerations, there has been continuing research effort to develop methods for recovering the valuable and reusable organic and inorganic components of the said filtrate waste byproduct stream.

U.S. Pat. No. 3,726,888 describes a process for the separation and recovery of the components contained in the filtrate waste byproduct stream of an adipic acid manufacturing plant. The filtrate stream comprises a mixture of adipic acid, glutaric acid, succinic acid, nitric acid and metal catalyst values. The separation and recovery process involves contacting the filtrate with alkanol, and extracting with a water-immiscible organic solvent to provide an organic phase containing the formed esters, and to provide an aqueous phase containing the nitric acid and metal catalyst values. Each of the phases is fractionated to separate the mixtures into useful components.

U.S. Pat. Nos. 4,076,948 and 4,082,788 describe processing improvements which are adapted to overcome some of the difficulties characteristic of the byproduct separation and recovery technology disclosed in the above recited U.S. Pat. No. 3,726,888.

One of the several problems associated with the production of methyl esters of $C_4$–$C_6$ carboxylic acid components (i.e., those acid components contained in the filtrate byproduct stream derived from adipic acid manufacture) is the accumulation of a residual bottoms fraction which results from the fractional distillation procedure for the recovery of refined dimethyl esters of succinic acid, glutaric acid and adipic acid.

If the residual bottoms fraction is recycled to the esterification step in the methyl ester production and recovery process, the heavy organic components of the said residual bottoms fraction cause fouling of the esterification and extraction equipment employed in the process. For this reason the described residual bottoms fraction normally is disposed of as a waste stream by burning or dumping.

There remains a need for new technology to improve economic and environmental aspects of adipic acid production by increased conversion of the filtrate waste stream into useful products.

Accordingly, it is a main object of this invention to improve the efficiency of an adipic acid manufacturing operation by recovery of byproduct values.

It is another object of this invention to provide a process for improving the material balance associated with the separation and recovery of $C_4$–$C_6$ dicarboxylic acids contained in a filtrate byproduct stream derived from an adipic acid manufacturing operation involving nitric acid oxidation of cyclohexanone and/or cyclohexanol.

Other objects and advantages of the present invention shall become apparent from the accompanying description and illustrated data.

DESCRIPTION OF THE INVENTION

As noted previously, in the oxidation of cyclohexanone and/or cyclohexanol with nitric acid in the presence of a metal oxidation catalyst, the resulting oxidation product solution is processed for recovery of the bulk of the desired adipic acid by crystallization and filtration. The acidic mother liquor (i.e., the aqueous filtrate byproduct stream) contains quantities of monobasic and dibasic carboxylic acids as well as nitric acid and metal catalyst values. These filtrate components are sufficiently valuable to encourage the application of recovery procedures.

A typical filtrate byproduct stream nominally corresponds to the following weight percent composition:

| Component | Amount |
| --- | --- |
| Succinic acid | 3–10% |
| Glutaric acid | 8–35% |
| Adipic acid | 3–6% |
| Nitric acid | 6–20% |
| Catalyst | 1–3% |
| Water | Balance |

The catalyst values contained in the filtrate are those which are conventionally employed in cyclohexanone/cyclohexanol oxidation procedures, such as copper, vanadium, and the like.

The present invention process is adapted to improve the material balance associated with the separation and recovery of $C_4$–$C_6$ dicarboxylic acids which are contained in the said filtrate byproduct stream of an adipic acid manufacturing operation. The invention process is particularly applicable to a $C_4$–$C_6$ dicarboxylic acid separation and recovery method which proceeds via in intermediate ester formation step.

Thus, one or more objects of the present invention are accomplished by the provision of an improved process for producing methyl esters of $C_4$–$C_6$ carboxylic acid components contained in an aqueous filtrate, which filtrate is a waste byproduct stream derived from the production of adipic acid by nitric acid oxidation of cyclohexanone/cyclohexanol, wherein the said process comprises the steps of admixing the filtrate byproduct stream with methanol and heating the admixture to form methyl esters of the $C_4$–$C_6$ carboxylic acid components, extracting the methyl ester components by contacting the esterification medium with a water-immiscible organic solvent, and separating the immiscible organic solvent phase and aqueous phase, the improvement which comprises (1) distilling the said organic solvent phase to yield dimethyl esters of succinic acid, glutaric acid and adipic acid, and a residual bottoms fraction; (2) admixing the said bottoms fraction with methanol to dissolve $C_4$–$C_6$ carboxylic acids and methyl esters and to precipitate heavy organic components which are methanol-insoluble; and (3) separating the methanol solution phase and recycling it to esterification step (2) of the process.

The initial esterification and solvent extraction stages of the process are described more fully hereinafter in connection with two preferred embodiments of the invention.

With reference to the improvement aspects of the invention process, in step (1) as indicated in the above definition, the recovered organic solvent phase is fractionally distilled to isolate refined dimethyl esters of succinic acid, glutaric acid and adipic acid. The dimethyl esters may be recovered either as a mixture of esters or as individual species.

The distillation of the organic solvent phase concomitantly produces a residual bottoms fraction. This said bottoms fraction contains higher boiling components which include succinic acid, glutaric acid, adipic acid, and monomethyl esters thereof. The bottoms fraction normally will contain a small quantity of relatively nonvolatile components such as oils and resins.

In step (2) of the above-described process embodiment, the bottoms fraction is thoroughly admixed with methanol at a temperature between about 0° C.–60° C. for a period of time between about 0.5–15 minutes which is sufficient to effect substantial partition between methanol-soluble and methanol-insoluble components of the said bottoms fraction. The quantity of methanol employed can vary in the range between about 0.5–5 volumes of methanol, preferably between about 0.8–4 volumes, per volume of the bottoms fraction.

In step (3) of the above-described process embodiment, the methanol solution phase containing the soluble components is separated from the heavy organic precipitate phase and recycled to the esterification step of the overall process. The separation of the two phases can be accomplished by centrifugation, decantation, filtration, and the like. A flocculating agent or filtering aid may be added to the step (3) admixture to facilitate the separation procedure.

The recycled methanol solution contains the methanolsoluble components of the bottoms fraction which include succinic acid, glutaric acid, adipic acid, and the monomethyl esters of these acids. The methanol solution also contains residual amounts of dimethyl esters of the same acids, particularly dimethyl adipate.

The heavy organic material which is recovered as a methanol-insoluble fraction in step (3) of the process is withdrawn from the system as a waste byproduct. This fraction represents only a minor quantity of material and is readily disposable by burning, and the like.

The practice of the present invention as a continuous process can be better understood by reference to the accompanying drawing which is illustrated as a flow diagram.

In the drawing, a filtrate stream is fed through line 10 into Esterification unit 15. Methanol is fed into Esterification unit 15 via line 16, and the esterification reaction is conducted at a temperature of 70° C. for a period of about 15 minutes to form methyl esters of $C_4$–$C_6$ carboxylic acids.

The esterification reaction medium is withdrawn continuously from esterification unit 15 through line 17 and introduced into Extraction unit 20. An organic solvent (e.g., benzene) is fed countercurrently into Extraction unit 20 by means of line 21. The extraction cycle is conducted at a temperature of 70° C. for a contact time of about 5 minutes.

The organic solvent phase is recovered from Extraction unit 20 and passed through line 22 into Water Wash unit 25, and there it is contacted countercurrently with water which is fed through line 26 into Water Wash unit 25.

The aqueous phase is recovered from Extraction unit 20 and passed through line 27 into Methanol Stripping unit 30. The stripped methanol from unit 30 is cycled to Precipitation unit 35 through line 32, and the residual aqueous nitric acid solution and the catalyst values contained therein is recycled from unit 30 to the adipic acid production unit through line 33.

The spent water wash effluent from Water Wash unit 25 is recycled through line 28 to Extraction unit 20. The water washed organic solvent stream is recovered from Water Wash unit 25 and passed through line 29 into Solvent Stripping unit 40. The stripping organic solvent from unit 40 is recycled to Extraction unit 20 via line 41.

A refined mixed dimethyl ester fraction is withdrawn from Solvent Stripping unit 40 through line 42, and charged to Fractional Distillation unit 45. Lines 46, 47 and 48 are employed to isolate pure dimethyl succinate, dimethyl glutarate and dimethyl adipate, respectively.

The residual bottoms fraction is withdrawn from unit 45 through line 49 and fed into Precipitation unit 35. Methanol is charged through line 50 to Precipitation unit 35, in a volume which is approximately equal to the volume of the bottoms stream. The contact time between the methanol and bottoms stream is maintained for a period of about two minutes at a temperature of about 40° C. The methanol extraction medium and the precipitated solids suspended therein are passed through line 51 into Filter unit 55. The methanol filtrate is recovered from unit 55 through line 56 and recycled to Esterification unit 15.

In a preferred embodiment, this invention contemplates a process for producing methyl esters of $C_4$–$C_6$ carboxylic acid components contained in an aqueous filtrate, which filtrate is a waste byproduct stream derived from the production of adipic acid by nitric acid oxidation of cyclohexanone/cyclohexanol, the improvement which comprises the steps of (1) concentrating the volume of the aqueous filtrate medium by the removal of excess water and the volatile components which co-distill with water to provide a concentrate solution; (2) admixing the concentrate solution with methanol, and heating the solution at a temperature between about 60° C.–90° C. to form methyl esters of the $C_4$–$C_6$ carboxylic acid components; (3) extracting the methyl ester components by contacting the esterification medium with a water-immiscible organic solvent at a temperature between about 40° C.–90° C.; (4) separating the immiscible organic solvent phase and aqueous phase; (5) fractionally distilling the organic solvent phase from step (4) to yield a mixed dimethyl ester fraction, and a residual bottoms fraction; (6) admixing the said bottoms fraction with methanol to dissolve $C_4$–$C_6$ carboxylic acids and methyl esters and to precipitate heavy organic components which are methanol-insoluble; and (7) separating the methanol solution phase and recycling it to esterification step (2) of the process.

In another preferred embodiment, this invention contemplates a method for producing dimethyl esters of $C_4$–$C_6$ carboxylic acid components contained in an aqueous filtrate, which filtrate is a waste byproduct stream derived from a process for producing adipic acid by nitric acid oxidation of cyclohexanone/cyclohexanol, the improvement which comprises the steps of (1) concentrating the volume of the aqueous filtrate medium by the removal of water and the volatile components which co-distill with water to provide a concentrate solution which has a water content between about 5–30 weight percent and a nitric acid content between about 1–6 weight percent, based on total solution weight; (2) admixing the concentrate solution with between about 20–60 weight percent methanol, based on total solution weight, and heating the solution at a temperature between about 60° C.–90° C. to form methyl esters of the $C_4$–$C_6$ carboxylic acid components; (3) extracting the methyl ester components by contacting the esterification medium with a water-immiscible organic solvent at a temperature between about 40° C.–90° C.; (4) separating the immiscible organic solvent phase and aqueous phase; (5) concentrating the aqueous phase from step (4) by distillation to provide a residual aqueous solution containing nitric acid and metal catalyst values; (6) fractionally distilling the organic solvent phase from step (4) to yield dimethyl esters of succinic acid, glutaric acid and adipic acid, and a residual bottoms fraction; (7) admixing the said bottoms fraction with methanol to dissolve $C_4$–$C_6$ carboxylic acids and methyl esters and to precipitate heavy organic components which are methanol-insoluble; and (8) separating the methanol solution phase and recycling it to esterification step (2) of the process.

In the two preferred embodiments described above, a particularly important aspect is the step (1) concentration of the volume of the aqueous filtrate medium by the removal of water and nitric acid, and other volatile components which co-distill with water. The volatile components which co-distill with the water and nitric acid include butyric acid, valeric acid and caproic acid.

Several advantages derive from the step (1) concentration of the aqueous filtrate byproduct stream.

First, the reduced volume of the filtrate medium permits the use of smaller capacity equipment for the subsequent esterification and extraction steps of the process.

Second, the reduced proportion of water in the filtrate concentrate solution causes a favorable equilibrium shift toward ester formation in the step (2) esterification reaction.

Third, the removal of monobasic acids during the step (1) concentration of the filtrate byproduct stream facilitates the production and recovery of dimethyl esters having improved color and odor specifications.

Fourth, the removal of nitric acid during the step (1) concentration of the filtrate byproduct stream has the important advantage of reducing the level of methyl nitrite and methyl nitrate byproduct formation during the step (2) esterification. The formation of these byproducts is primarily a function of the nitric acid concentration. These byproducts are undesirable because they cause the loss of both methanol and nitric acid. Further, these byproducts tend to be unstable and represent a potential explosion hazard. They must be purged periodically from the process system.

Fifth, the recovery of nitric acid during the step (1) concentration phase permits a highly efficient recycle of the said nitric acid to the cyclohexanone/cyclohexanol oxidation system.

With reference to step (2) of the two preferred embodiments, a unique fixture of the esterification reaction is the rate efficiency with which equilibrium is achieved between the esterified and unesterified dicarboxylic acid components, even in the presence of a highly dilute aqueous nitric acid solution. The efficiency of the step (2) esterification reaction is attributable to a combination of controlling factors, such as an elevated reaction temperature, a high proportion of methanol relative to a low proportion of water, the absence of interfering byproduct components (e.g., monocarboxylic acids), and the like.

The step (2) esterification reaction time on the average will vary in the range between about 5–25 minutes, depending on the temperature maintained in the esterification zone.

In a similar manner, the combination of delimiting parameters of the step (3) extraction stage of the two preferred embodiments provides technical advantages. Hence, an extraction temperature in the range between about 40° C.–90° C. has the beneficial effect of accelerating the additional conversion of free carboxylic acids to methyl ester derivatives. Substantially complete transfer of dimethyl esters into the organic solvent phase is achieved during the step (3) extraction period. This efficient extraction of dimethyl esters by the organic solvent is readily accomplished within a phase contact period between about 2–20 minutes.

The quantity of water-immiscible organic solvent employed in the step (3) extraction stage usually will vary in the range between about 0.5–2 volumes per volume of esterfication medium being extracted, and on the average will approximate a volume ratio of 1:1.

A preferred type of water-immiscible organic solvent is one selected from aromatic hydrocarbons, aliphatic hydrocarbons, cycloaliphatic hydrocarbons, halogenated aliphatic hydrocarbons, and halogenated aromatic hydrocarbons. Particularly preferred species include cyclohexane, benzene, toluene, xylene, ethylbenzene, chloroform, o-dichlorobenzene, and the like.

Because of the elevated up to 90° C. temperature employed during the esterification and extraction steps of the two preferred embodiments, equipment is employed which is adapted for 15–100 psi reaction systems.

At the end of the step (3) extraction period, the immiscible organic solvent and aqueous phases are separated and individually recovered in step (4) for subsequent manipulative procedures.

In a particularly preferred procedure, the recovered organic solvent phase is contacted with wash water in a manner sufficient to remove substantially all of the methanol and residual nitric acid components present in the organic solvent phase, and to reduce the free carboxylic acids and monomethyl esters of dicarboxylic acids content of the organic solvent phase. The water washing step facilitates the subsequent recovery of high quality organic byproducts.

The said organic solvent phase from step (4) is distilled to strip the solvent medium, and yield a refined mixed dimethyl ester fraction. The said ester mixture can be employed directly to prepare high molecular weight esters applicable as plasticizers for polyvinyl chlorides. Alternatively, the ester mixture can be further fractionated to yield pure dimethyl succinate, dimethyl glutarate and dimethyl adipate, respectively. If desired, the dimethyl esters can be hydrolyzed to the corresponding high purity acids.

With respect to the aqueous phase which is separated and recovered in step (4) after the step (3) extraction operation, the said aqueous phase is subjected to concentration in vacuo to remove the dissolved methanol content and to provide a residual aqueous solution containing nitric acid and copper/vanadium type metal values. The said residual aqueous solution is suitable for recycle to the cyclohexanone/cyclohexanol oxidation system.

The two preferred embodiments described above can be conducted as a continuous process. The two process embodiments can be operated in accordance with the flow diagram illustrated in the drawing, except that a concentrated filtrate is fed through line 10.

The following examples are further illustrative of the present invention. The reactants and other specific ingredients are presented as being typical, and various modifications can be derived in view of the foregoing disclosure within the scope of the invention.

EXAMPLE I

This Example illustrates the advantages of the present invention process for recovery of byproducts associated with the isolation of $C_4$–$C_6$ dicarboxylic acids contained in a waste byproduct stream from an adipic acid manufacturing operation.

A product mixture is recovered from nitric acid oxidation of a cyclohexanone/cyclohexanol starting material. The product mixture is cooled, and crystalline adipic acid is separated by filtration.

The mother liquor is then subjected to the steps of the present invention process as illustrated in the drawing. The residual bottoms fraction from the fractional distillation operation is admixed with methanol in a ratio of about 3 volumes of methanol per volume of bottoms fraction. The mixture is stirred for about 5 minutes at an ambient temperature of about 20° C.

A black semi-solid material separates as a suspension in the methanol medium. The suspended material is then removed by filtration, and it constitutes about 2 weight percent of the bottoms fraction being treated.

The filtered methanol solution is recycled and employed as feed material in admixture with a quantity of the original adipic acid filtration mother liquor. No insoluble solids separate out during the subsequent esterification and extraction steps.

The above described procedure is repeated, except that the residual bottoms fraction from the fractional distillation step is recycled directly to the esterification step, without any precipitation/filtration pretreatment of the bottoms fraction as provided by the present invention process.

During the extraction of the aqueous esterification medium with benzene solvent, a black semi-solid material separates out and causes fouling of the extraction column.

EXAMPLE II

This Example illustrates the present invention process in which a concentrated adipic acid byproduct mother liquor is employed as the starting feedstream.

A filtrate byproduct stream (i.e., waste mother liquor) from an adipic acid manufacturing plant is distilled at subatmospheric pressure to reduce the water and nitric acid contents of the mixture and provide a concentrate solution.

The concentrate solution contains about 70 weight percent of adipic, glutaric and succinic acids. The other main components comprise about 5 weight percent nitric acid, 20 weight percent water, and about 1.0 weight percent copper and 500 ppm of vanadium.

A mixture of esterification reactants is prepared which has the following composition:

|  | Grams |
| --- | --- |
| Filtrate concentrate | 4846 |
| Methanol | 3368 |
| Nitric acid, 70% | 301 |
| Residual bottoms | 2536 |

The residual bottoms material is the fraction which is recovered from the fractional distillation column as illustrated in the drawing. The fraction contains monomethyl esters of succinic acid, glutaric acid and adipic acid, and additionally contains some nonvolatile oils and resins. The residual bottoms material being employed is not pretreated to remove the heavy ends.

The esterification reaction mixture is stirred for one hour at 60° C. The resultant product mixture is fed into a glass extraction column which is packed with porcelain saddles.

The extraction column contains a 36 inch packed section. The column is thermostated at 60° C. and operates at a pressure of about 15 psig. The esterification feed is entered continuously into the extraction column at a point six inches below the top of the packed section. Benzene is fed continuously to the bottom of the extraction column, and water is fed continuously to the top of the extraction column. The function of the water is to wash methanol, nitric acid and catalyst values from the benzene phase during the extraction operation.

The volume ratio of benzene to esterification feed in the extraction column is 1:1.5, and the contact time between the two phases is about 10 minutes.

During the extraction operation, the extraction column packing became fouled with a deposit of black material. Subsequently, this material is found to be insoluble in each of water, benzene and methanol.

The benzene phase is recovered, and distilled to a pot temperature of 175° C. at a pressure of 70 mm of mercury. The distillate product is substantially dimethyl esters of adipic acid, glutaric acid and succinic acid.

The distillation column bottoms (1936 grams) is diluted with methanol (6093 grams) at ambient temperature. A black semi-solid material precipitates in the form of a suspension, and is removed by filtration. The resultant methanol filtrate is clear and has a light straw color.

The following mixture of esterification reactants is prepared:

|  | Grams |
| --- | --- |
| Methanol filtrate | 7850 (est.) |

|  | Grams |
| --- | --- |
| Filtrate concentrate | 10608 |
| Nitric acid, 70% | 467 |
| Methanol | 1553 |

The esterification and extraction steps are performed in the same manner as described above. There is no evidence of insoluble black precipitate in either the esterification unit or in the extraction column.

What is claimed is:

1. In a process for producing methyl esters of $C_4$-$C_6$ carboxylic acid components contained in an aqueous filtrate, which filtrate is a waste byproduct stream derived from the production of adipic acid by nitric acid oxidation of cyclohexanone/cyclohexanol, wherein the said process comprises the steps of admixing the filtrate byproduct stream with methanol and heating the admixture to form methyl esters of the $C_4$-$C_6$ carboxylic acid components, extracting the methyl ester components by contacting the esterification medium with a water-immiscible organic solvent, and separating the immiscible organic solvent phase and aqueous phase, the improvement which comprises (1) distilling the said organic solvent phase to yield dimethyl esters of succinic acid, glutaric acid and adipic acid, and a residual bottoms fraction; (2) admixing the said bottoms fraction with methanol to dissolve $C_4$-$C_6$ carboxylic acids and methyl esters and to precipitate heavy organic components which are methanol-insoluble; and (3) separating the methanol solution phase and recycling it to the esterification step of the process.

2. A process in accordance with claim 1 wherein about 20-60 weight percent methanol, based on total solution weight, is employed in the esterification step.

3. A process in accordance with claim 1 wherein the esterification step is conducted at a temperature between about 60° C.-90° C.

4. A process in accordance with claim 1 wherein the water-immiscible solvent employed in the extraction step is selected from aromatic hydrocarbons, aliphatic hydrocarbons, cycloaliphatic hydrocarbons, halogenated aliphatic hydrocarbons and halogenated aromatic hydrocarbons.

5. A process in accordance with claim 1 wherein the water-immiscible solvent employed in the extraction step is benzene.

6. A process in accordance with claim 1 wherein the components dissolved in methanol in step (2) consist substantially of succinic acid, glutaric acid, adipic acid, and monomethyl esters thereof.

7. A process in accordance with claim 1 wherein the methanol medium in step (2) is employed in a quantity between about 0.8-4 volumes per volume of the said bottoms fraction.

8. A process in accordance with claim 1 wherein the step (2) methanol treatment is conducted at a temperature between about 0° C.-60° C. for a period of time between about 0.5-15 minutes sufficient to achieve partition between methanol-soluable and methanol-insoluble components of the said bottoms fraction.

9. A process in accordance with claim 1 wherein the step (3) separation of the methanol solution phase from the heavy organic precipitate is accomplished by filtration.

10. In a process for producing methyl esters of $C_4$-$C_6$ carboxylic acid components contained in an aqueous filtrate, which filtrate is a waste byproduct stream derived from this production of adipic acid by nitric acid oxidation of cyclohexanone/cyclohexanol, the improvement which comprises the steps of (1) concentrating the volume of the aqueous filtrate medium by the partial removal of water and the volatile components which co-distill with water to provide a concentrate solution; (2) admixing the concentrate solution with methanol, and heating the solution at a temperature between about 60° C.-90° C. to form methyl esters of the $C_4$-$C_6$ carboxylic acid components; (3) extracting the methyl ester components by contacting the esterification medium with a water-immiscible organic solvent at a temperature between about 40° C.-90° C.; (4) separating the immiscible organic solvent phase and aqueous phase; (5) fractionally distilling the organic solvent phase from step (4) to yield a mixed dimethyl ester fraction, and a residual bottoms fraction; (6) admixing the said bottoms fraction with methanol to dissolve $C_4$-$C_6$ carboxylic acids and methyl esters and to precipitate heavy organic components which are methanol-insoluble; and (7) separating the methanol solution phase and recycling it to esterification step (2) of the process.

11. In a method for producing dimethyl esters of $C_4$-$C_6$ carboxylic acid components contained in an aqueous filtrate, which filtrate is a waste byproduct stream derived from a process for producing adipic acid by nitric acid oxidation of cyclohexanone/cyclohexanol, the improvement which comprises the steps of (1) concentrating the volume of the aqueous filtrate medium by the removal of water and the volatile components which co-distill with water to provide a concentrate solution which has a water content between about 5-30 weight percent and a nitric acid content between about 1-6 weight percent, based on total solution weight; (2) admixing the concentrate solution with between about 20-60 weight percent methanol, based on total solution weight, and heating the solution at a temperature between about 60° C.-90° C. to form methyl esters of the $C_4$-$C_6$ carboxylic acid components; (3) extracting the methyl ester components by contacting the esterification medium with a water-immiscible organic solvent at a temperature between about 40° C.-90° C.; (4) separating the immiscible organic solvent phase and aqueous phase; (5) concentrating the aqueous phase from step (4) by distillation to provide a residual aqueous solution containing nitric acid and metal catalyst values; (6) fractionally distilling the organic solvent phase from step (4) to yield dimethyl esters of succinic acid, glutaric acid and adipic acid, and a residual bottoms fraction; (7) admixing the said bottoms fraction with methanol to dissolve $C_4$-$C_6$ carboxylic acids and methyl esters and to precipitate heavy organic components which are methanol-insoluble; and (8) separating the methanol solution phase and recycling it to esterification step (2) of the process.

12. A process in accordance with claim 11 wherein the residual aqueous solution provided by step (5) is recycled to the primary cyclohexanone/cyclohexanol oxidation stage of the process.

13. A process in accordance with claim 1 wherein the step (3) separation of the methanol solution phase from the heavy organic precipitate is accomplished by decantation.

* * * * *